(12) United States Patent  
Jackson

(10) Patent No.: US 8,420,401 B2
(45) Date of Patent: Apr. 16, 2013

(54) GLUCOSE TOLERANCE TEST DEVICE

(75) Inventor: James Jackson, Oxfordshire (GB)

(73) Assignee: SmartSensor Telemed Limited, Oxfordshire (GB)

( * ) Notice: Subject to any disclaimer, the term of this patent is extended or adjusted under 35 U.S.C. 154(b) by 212 days.

(21) Appl. No.: 12/733,290

(22) PCT Filed: Aug. 22, 2008

(86) PCT No.: PCT/GB2008/002853  
§ 371 (c)(1),  
(2), (4) Date: May 4, 2010

(87) PCT Pub. No.: WO2009/024794  
PCT Pub. Date: Feb. 26, 2009

(65) Prior Publication Data  
US 2010/0240079 A1 Sep. 23, 2010

(30) Foreign Application Priority Data  
Aug. 23, 2007 (GB) .................................. 0716427.0

(51) Int. Cl.  
*G01N 33/48* (2006.01)

(52) U.S. Cl.  
USPC ................. 436/95; 436/50; 436/63; 422/403; 422/430; 422/68.1

(58) Field of Classification Search ............... 422/403, 422/430, 68.1; 436/50, 63, 95  
See application file for complete search history.

(56) References Cited

U.S. PATENT DOCUMENTS

| 4,731,726 | A | 3/1988 | Allen |
| 5,837,546 | A | 11/1998 | Allen et al. |
| 7,118,919 | B2 | 10/2006 | Yatscoff et al. |
| 2001/0031913 | A1 | 10/2001 | Ito et al. |
| 2003/0211617 | A1 | 11/2003 | Jones |
| 2003/0212379 | A1 | 11/2003 | Bylund et al. |
| 2005/0090726 | A1 | 4/2005 | Ackerman |
| 2006/0178600 | A1 | 8/2006 | Kennedy et al. |

FOREIGN PATENT DOCUMENTS

| EP | 1 338 295 A1 | 8/2003 |
| JP | 2001-221803 | 8/2001 |
| WO | WO 99/56790 | 11/1999 |
| WO | WO 03/071940 A1 | 9/2003 |

*Primary Examiner* — Lyle Alexander  
(74) *Attorney, Agent, or Firm* — Jacobson Holman PLLC

(57) ABSTRACT

A glucose tolerance test device comprising: a test zone having a means to receive at least first and second blood test samples spaced apart by a predetermined time interval; a timer to measure such a time interval, and for example to measure elapsed time after collection of a said first sample; an indicator to indicate at least that a second test is due, operatively Jinked to the timer so as to make such indication after lapse of a predetermined time interval; a data collector to collect data from the lest zone in relation to each test sample; a data register to store data in relation to each test sample, in data communication with said data collector. A method of use is also described.

11 Claims, 2 Drawing Sheets

GLUCOSE TOLERANCE TEST DEVICE

This is a national stage of PCT/GB08/002853 filed Aug. 22, 2008 and published in English, which has a priority of United Kingdom no. 0716427.0 filed 23 Aug. 2007, hereby incorporated by reference.

The invention relates to a glucose tolerance test device and to a method of use therefor, and in particular to a device adapted to simplify administration of a predetermined glucose tolerance test protocol, for example to facilitate domestic use without the requirement for direct clinical supervision.

In accordance with a typical glucose tolerance test protocol, a patient is required to fast for a period, for example overnight, before commencement of the protocol. The patient then typically attends a medical centre where, under clinical supervision, a first blood test is taken, and passed for analysis and the results recorded. After the sample has been taken the patient is then given a glycaemic load to ingest, for example in the form of a drink or solid food stuff adapted to deliver a predetermined glycaemic load. On expiration of a predetermined waiting time appropriate to the particular protocol being followed, a second blood sample is taken and analysed in similar manner to the first blood sample, and the results recorded. Further blood samples after further time periods may also be taken. In general, it is desirable that the patient minimizes movement and physical activity between test samples.

A comparison of the results of the respective blood samples, and in particular the glucose levels therein, taken together with the time periods and other data for example concerning the glycaemic load, may be used to determine the glycaemic status of the patient in familiar manner.

In contrast to the simple glucose level tests which diabetic patients generally take in a domestic environment, often several times a day and as a matter of routine, by obtaining a finger prick blood spot or the like, glucose tolerance tests are carried out only occasionally and on an ad hoc basis at the requirement of a supervising physician. Conventionally, a normal glucose tolerance test protocol involves supervision by a medical practitioner, and for example attendance at a medical centre, at least for the taking of blood before and after ingestion of the glycaemic load, and for the development and analysis of the results, which typically involves a more detailed consideration of a broader range of parameters than might be the case for a single simple routine glucose test carried out domestically. This requirement for the protocol to be practitioner led, and in many instances to be carried out at a medical facility can be a source of inconvenience for patients and healthcare professionals and limits the resources available to perform the test.

It is an object of the invention to provide a glucose tolerance test device and method of use which mitigates some or all of the problems with existing testing devices and protocols especially in relation to the collection of data.

It is a particular object of the invention to provide a device which is adapted to simplify administration of a predetermined glucose tolerance test data collection protocol, for example to facilitate use in a domestic environment and/or in a manner which reduces the need for direct clinical supervision.

Thus, in accordance with the invention in a first aspect there is provided a tolerance test data collection device for testing glucose tolerance comprising: a test zone having a means to receive at least first and second blood test samples spaced apart by a predetermined time interval; a timer to measure such a time interval, and for example to measure elapsed time after collection of a said first sample; an indicator to indicate at least that a second test is due, operatively linked to the timer so as to make such indication after lapse of a predetermined time interval; a data collector to collect data from the test zone in relation to each test sample; a data register to store data in relation to each test sample, in data communication with the said data collector.

The device of the invention is specifically adapted to implement a particular glucose tolerance testing protocol and to collect data in accordance with the protocol. An example protocol is described hereinafter by way of illustration of the device.

In accordance with the protocol, a user first fasts for a specified time period, for example at least eight hours fasting overnight, as specified by instructions accompanying the glucose tolerance test device of the invention and/or on the instruction of an advising medical or other supervising practitioner.

The user then obtains a blood drop sample, for example via a finger prick test by means of a lancet in familiar manner, and adds this sample to a test zone. The data collector collects data concerning the sample in the test zone, and this is communicated to the data register for storage.

The user then ingests a standardised glycaemic load for example in the form of a glucose drink.

Following ingestion of the standardised glycaemic load, the user is intended to wait a predetermined time interval before carrying out one or more subsequent blood tests, for example as specified by instructions accompanying the device or by the instruction of an advising medical or other supervising practitioner. The timer of the device of the invention is adapted to measure an elapsed time interval and to function co-operatively with the indicator to indicate at least, expiry of this time interval. The timer may be adapted to mark commencement of the predetermined time interval and begin to measure the same automatically on performance of the first test when a first blood sample is placed in a test zone. Alternatively, means may be provided to allow the user to start the process of timing the predetermined interval, for example by means of a user operable start control, such as a start button. This alternative is particularly preferred, since it gives a user flexibility over timing. For example a user may start the timing process on ingestion of the standard glycaemic load, the button thus constituting a "confirm glycaemic load ingestion" button and/or a user may start the timing process from the blood spot addition.

The user waits the predetermined time interval before performing at least one further blood test. The indicator acts in conjunction with the timer to provide an indication at least on expiration of the predetermined wait time and thus an indication that the next test is due. In response to this indication the user obtains a second blood drop sample, in similar manner to the first, and supplies this to a test zone on the glucose tolerance test device.

Optionally, immediately on expiration of one or more further predetermined wait times, as indicated by the test device and its accompanying instructions or by the instruction of an advising medical or other supervising practitioner, a user may obtain further blood samples in the manner of the first blood sample and add each blood sample in turn to a test zone on the glucose tolerance test device.

In all such instances of a subsequent test, the user waits for a suitable test time until the glucose tolerance test device has concluded a test procedure. The test device may include a test completed indicator, or the requirements for the test to be concluded may be provided in accompanying instructions. The test protocol is then complete.

The device of the invention facilitates performance of a glucose tolerance test protocol in a simple compact device which is adapted to take a standard routine finger prick blood spot and which is adapted to guide a user through the most necessary steps of the protocol. In this way, by enabling a user to take their own blood sample via the finger prick procedure with which a diabetic user will be routinely familiar, and by controlling the basic timing of the protocol and guiding the user in following it accurately, the device enables a user to perform a basic glucose tolerance test protocol and collection of the test data at home and without direct clinical supervision with little more difficulty than the user will be familiar with from routine blood glucose level tests. The process is much simplified. The ability offered by the invention to perform a simple but still reasonably representative glucose tolerance test protocol in a domestic environment offers similar advantages to those offered by simple blood glucose level tests, reducing the time taken and the clinician involvement at the initial data collection stage of procedure.

In accordance with the invention, the timer is adapted at least to measure a specified first time predetermined interval in order to work in conjunction with the indicator to indicate when a second test is due. As noted, this time interval may commence automatically when a first sample is placed in a sample collection area, or may commence in response to a user input, for example input by a user once the glycaemic load has been consumed. In the case where the time period is automatically started by the device after the first sample is recorded, an optional featue of the device is that the user may also indicate that the drink has been taken, for example by depressing the confirmation button, but that this will not be registered as the commencement time, rather it will only serve to provide the user with a way of confirming that the glycaemic load has been consumed.

In a preferred embodiment, the timer additionally measures at least a first elapsed time between performance of the first test, when a first sample is placed in a sample collection area, and/or when the time interval start control is actuated and performance of the second test, when a second sample is placed in a sample collection area. In this manner the actual elapsed time before the second test is taken is specifically measured, so that if a user is late in reacting to a test due indicator specific timing data is collected. To facilitate this, the timer is in data communication with the data register which is further adapted to store such time interval data. A test zone includes a means to detect the presence of a sample in a sample collection area, and thus to indicate when a test is performed.

It will be clearly understood herein that where reference is made to a second test, it could equally apply to subsequent tests in the case where a protocol requires a plurality of subsequent tests. In such cases a timer may measure one or more specified predetermined further time intervals and/or one or more further elapsed times as the case may be.

The or each predetermined time interval may be preloaded into a memory register within the device, or may be input by suitable input means. These may be set by a clinician or other supervisor of the protocol at the outset, or may be user settable, for example in accordance with such a supervisor's instructions or otherwise.

Where reference is made herein to a parameter being presettable or being suitable for input, it will be appreciated that this could be done by a supervising clinician or other supervisor, or by an end user. The device of the invention may be provided with, or adapted to be placed in data communication with, a suitable input means. Alternatively, any such parameter may be inherently pre-set in a memory register comprised as a part of the device.

A test zone is adapted for the collection of at least two successive samples over at least one predetermined specified time interval, and optionally of a larger plurality of successive samples spaced apart by a plurality of predetermined intervals. A test zone includes one or more sample collection areas for receiving a blood sample for analysis by the data collector. A sample is a blood sample, and in particular a pin prick blood sample for example produced by a finger prick procedure. A sample collection area therefore preferably comprises a sample collection well to retain such a fluid sample in situ during performance of the test in fluid communication with a suitable means to provide for data collection. A sample collection well for example comprises an apertured or structured portion in a device body defining a receptacle structure into which a sample can be received and retained for testing. For example a sample collection well constitutes a circular aperture or structure in the body of the device defining such a sample retention area. The sample retention area may include a layer of absorbent material into which the sample can be absorbed in situ during performance of the test in familiar manner.

The device preferably includes one or more sample analysers. For example, a sample analyser is provided in association with (e.g. in fluid communication with) a test zone. Conveniently, a sample analyser may be located in a test zone. A sample analyser is for example an electrochemical biosensor, and may for example be of similar construction similar to those electrochemical biosensors used in test strips supplied with conventional glucose meters.

In order to collect plural samples a plurality of test zones and/or a plurality of sample collection areas may be defined and/or a plurality of sample analysers may be provided. Alternatively, a single test zone and/or a single sample collection area and/or optionally additionally a single sample analyser may be provided adapted for successive use by plural samples. Where plural sample collection areas are provided, these may be integral to the device, or they may be provided in the form of plural attachable and/or detachable sample collection modules, each defining at least a sample collection area, and an attachment portion to attach the module in data communicating manner to a receiving portion in the test device so as to form when so received a test zone in accordance with the invention.

In one embodiment, each sample collection module constitutes a separate attachable test strip which is attachable to the test device to provide a sample collection area in data communication with the rest of the device in use, but is detachable after performance of the test. Such a test strip arrangement will be familiar from similar test strips provided in relation to glucose test devices.

The use of such attachable test strips again exploits the simplicity with which a diabetic patient will be familiar from basic blood glucose testing. In particular, the use of separate test strips avoids direct blood contact with the device, which can be useful for hygiene purposes, and allows the device to be used for multiple tests. A plurality of test strips may be provided to perform a plurality of tests. Where plural test strips are provided, they may be exchangeable into a single receiving means in communication with a common data collector, or may be provided with separate receiving means communicating with discrete data collectors.

In an alternative embodiment, a plurality of detachable sample collection modules may be provided, one for each sample to be collected, initially as an integral part of the device of the invention but adapted to be detached, for example for hygiene reasons, once a sample has been processed on the sample collection area and data therefrom collected by the data collector.

The indicator in the device of the invention indicates at least that a predetermined time interval has completed, and that it is therefore time to perform a subsequent blood test in accordance with the protocol. The indicator may comprise an audio and/or a visual indication of the expiry of this time limit. More preferably, the indicator also provides an indication of the lapse of time as the time limit progresses, for example in some form of countdown. This may take the form of alphanumeric display, successive lights indicating progression of a time interval, electronically sensitive ink strips indicating progression of a time interval, or any other suitable combination. Preferably, the indicator is an audiovisual display and a visual display is given of the progress of the time interval and an audio alarm is given on its expiry.

The indicator may be further adapted to give other indications, and for example to indicate the completion of a particular step, such as the completion of an individual test.

A data collector is provided to collect data concerning the sample in use in a sample collection area, and in particular to collect data concerning the following: timing information relating to the addition of samples to the test device, for example the time and date, the temperature of the test device or its environment at the time of performing tests; test signals relating for example to the concentration of glucose in a test sample. Said test signals may be varied in nature, for example test signals may relate to electrical current, potential or capacitance, or may be optical, for example fluorescence. Where the device is adapted for the provision of a plurality of discrete test zones and/or discrete sample collection areas, an equivalent plurality of data collectors may be provided each in data communication with a single such zone or area, or the device may be adapted for a single data collector to analyse each zone or area successively as each test is performed.

A data register is provided to collect at least data from the data collector. Optionally, the register also stores additional data associated with the test procedure. For example, as above described, the data register may store data collected by the timer concerning time intervals between tests etc. The data register may record the time and/or the date of an event in which the test was commenced, or a particular stage of the test protocol was carried out. For example the data register may record the time and/or date that the test was commenced, the time and/or date of the addition of a first blood sample, the time and/or date when an actuation of a time interval control indicating consumption of the glycaemic load was made, the time and/or date indicating the addition of a second blood sample, the time and/or date of the addition of one or more further blood samples, relevant secondary data concerning each test procedure performed using the test zones of the glucose tolerance test device, for example recording test signals at predetermined time intervals, such as microamps each second for 20 seconds, recording the temperature of the test device of the time when each test signal reading was obtained etc.

To facilitate date and time recordal, the device may include a clock/calendar means, or the date and/or time may be input by a user. To facilitate temperature recordal, the device may include a temperature measuring and recording means, or the temperature may be input by a user. A user identification may be stored in the device which can be entered either by the user or by a medical practitioner.

A device of the invention may include, or be adapted to facilitate the download from the data register of data into, a suitable processing means to process the raw data collected by the data collector and stored in the data register, in order to effect calibration of the device and/or obtain clinically meaningful data, and for example diagnostic data, therefrom.

When the raw test data is collected, it should be calibrated using a specific algorithm which uses for example raw sensor data and temperature data. This can be done on the device but preferably is done externally in a separate instrument or database using a calibration algorithm matched to the particular device's data set. In an embodiment of the device in which the raw data is processed on-board the device to produce a test result, the result is stored within the device for display to the user and/or for upload to a remote database or the like.

Given the relatively complex nature of a glucose tolerance test analysis procedure (when compared for example with a simple blood glucose level test) it is often likely to be preferred if even though the data is collected domestically, the analysis step is performed by a clinician.

Accordingly, in a preferred embodiment the device is adapted both to collect data in a simple domestic environment under non-expert use and to allow the data to be readily passed to a clinical supervisor for processing.

For example, in one embodiment, to effect this, the device is provided in two parts, comprising a data collecting part including at least the test zone and for example also the data collector, and a recording part including at least the data register, the two parts being in data communication, but the data recording part being detachable from the data collecting part after use. In this way, the data recording part can be kept relatively small, and can be readily transported to a remote site for retrieval of data, while the data collecting part can be adapted either for reuse or discard.

In a preferred embodiment of the invention the recording part is selectively sized and shaped to facilitate handling and transport of the recording device to the relevant processing facility.

The above embodiment relates to a recording part that is sufficiently small and light to be transported via a conventional transport means for example, and not by way of limitation, the postal service or courier service.

In a possible embodiment of the invention a detachable recording part is provided in retro-fit form, i.e. it may be desirable to adapt a pre-existing data collection device to receive a recording part to enable data recording and storage.

It will be apparent from the above embodiment that the assessment device may be manufactured as a single unit. Alternatively, via suitable adaptation, said recording part or device may be attached to an existing data collection part or device to enable data recording.

Alternatively, the device, or the data recording part as the case may be, may be adapted to allow for electronic download of collected data to a remote site, for example in that it includes a data connection means to enable a communicating connection to a data network site such as an ethernet port, a serial or parallel port for connection to a computer, a port for connection to a wired or wireless telecommunications network for direct download, or any other suitable data connection link. Data transfer ideally will be encrypted to prevent third party access and decoded at a processing facility via responsible healthcare worker.

The data connection means also enables download of test protocol data and parameters. For example, such data would include the time interval between the first and second blood test. The data can be downloaded during an initialization procedure when the test device is first made operable, or download of data can be instigated by a user-initiated operation. In this way the device can be configured, for example, to test blood for gestational diabetes where the test time interval is 1 hour, or test blood for type 1 or type 2 diabetes where the test time interval is at least 2 hours. It should be understood that in practice the device can be configured for any test time interval.

In a preferred embodiment the recording device/part includes a microprocessor or other similar electronic device. Alternatively, the recording device is photographic, comprising, for example, a photographic emulsion, the stored images of which are developed at a processing facility. It is envisaged that the device can record data by known analogue photographic means or by known digital means, for example by employing a CCD, a photo detector, a photo-chemical detector or the like.

In yet a further preferred embodiment of the invention at least one control or calibration is provided in the assessing device. For example, a control conduit may be provided for monitoring flow through the device. Said control conduit may optionally be provided with assay reagents, or alternatively, the elements to be detected by the assay in order to produce a positive result or identification.

Conveniently, the test device may be fabricated to have a generally planar body, for example being fabricated from planar sheet-like material, which should be taken as to include its being folded, for example for compactness, and in particular being folded prior to use and unfolded for use. Any suitable sheet material can be used, and in particular cardboard or plastics material.

The sheet material, or at least an external surface thereof, preferably comprises fluid resistant material or is provided with a fluid resistant surface layer or laminated structure.

The device is preferably provided with accompanying instructions. An advantage of the sheet-like configuration is that at least some of these instructions may be printed upon a surface of the sheet in order to guide a user as to correct performance of the test protocol. However, the invention is not limited to a particular construction, and the device may be of any convenient construction, for example folded sheet, moulded plastic casing etc.

In accordance with a preferred aspect of the invention, the glucose tolerance test device comprises an element of a glucose tolerance test kit, being provided in combination with one or more of the following: a standardised glycaemic load; one or more test strips selectively attachable to the device to provide at least a sample collection area of a test zone; one or more lancets to obtain a finger prick sample from a user, for example in the form of a lancing pen; additional instructions for performance of successive tests in accordance with the predetermined protocol.

A standardised glycaemic load is preferably provided containing a specific and known amount of a predefined glycaemic substance, for example glucose. The standardised glycaemic load may be in the form of a pre-packaged think, or in the form of a powder which is to be added to a specified volume of liquid such as water to produce a drink, or incorporated into a solid food stuff.

In accordance with the invention in a further aspect there is provided a method of collecting data for performance of at least a data collection phase of a glucose tolerance test comprising the use of a device in accordance with the foregoing. The device of the invention is specifically adapted to implement a particular glucose tolerance testing protocol.

In accordance with the protocol of the method, a user carries out the following steps: fasts for a specified time period, for example at least eight hours fasting overnight; obtains a test device as above described; obtains a first blood spot sample, for example via a finger prick test by means of a lancet in familiar manner, and adds this sample to a test zone on the test device to obtain a first result; ingests a standardised glycaemic load; optionally following ingestion of a standardised glycaemic load operates a user operable control to indicate the start of a predetermined time interval; waits a predetermined time interval before performing at least one further blood test by obtaining at least one further blood sample, for example via a finger prick test by means of a lancet in familiar manner, and adding this sample to a test zone on the test device to obtain a further result.

It should be noted that in certain situations it is not necessary or required for the user to fast between tests.

At its most basic in connection with the foregoing, the method therefore comprises a method to perform a glucose tolerance test using the device of the invention up to the point where raw data is collected and stored in data register. In a further step, which is not part of the data collection process of the invention at its broadest embodiment, the data is analysed, by comparing test data from the at least two tests, and data concerning the predetermined time interval and/or a measured time interval between the carrying out of at least those two tests, and optionally further data such as described hereinabove, is analysed to produce clinically useful results and for example diagnostic results.

The analysis step may be performed domestically by a user with suitable data processing equipment. However, as set out hereinabove, the analysis step is preferably performed remotely and for example under more direct clinical supervision. The method of the invention may include the final step of supplying data collected as above for such a final analysis. In a preferred embodiment of the device, this is achieved in that the device comprises a detachable collecting/recording part, and the method comprises detaching the collecting/recording part and forwarding it to a medical third party for analysis of the stored data and/or processed results. Alternatively, the method comprises forwarding the data for analysis by other means, for example electronically, and for example by downloading the data in the data register by a suitable electronic communication means.

Alternatively, it is envisaged that the on-board processor of the collecting/recording part includes software or a suitable algorithm to enable the recorded raw test data to be converted into an actual test result(s) that is then stored on the device. Subsequently, the test result(s) can be either displayed to the user via the device display and/or up-loaded to a remote database to which the medical practitioner concerned has access.

Further preferred features of the method will be understood by analogy with the description of the use of the device hereinabove.

The invention will now be described by way of example only with reference to FIGS. 1 to 3 of the accompanying drawings in which.

Figure 1:
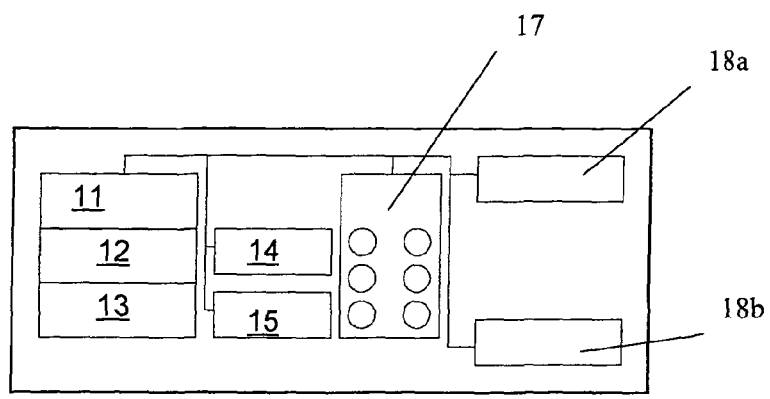
FIG. 1 is a schematic of one alternative arrangement of device.

Referring to the Figures, FIG. 1 represents a simple schematic of one possible embodiment of the invention. In this embodiment, a device that provides for a test protocol involving two blood tests spaced apart by a suitable time interval at the commencement of which a standard glycaemic load will be ingested is shown. Separate areas are provided for the placement of each test sample. The test areas are included integrally in the device.

The glucose tolerance test device thus includes two test areas (18a) and (18b) allowing for discrete application of a blood sample respectively before and after the interval period. Each test area includes an analytical means containing reagents required for the performing of a glucose test. Said analytical means may be in the form of an electrochemical biosensor. The remaining modules are provided for data processing, input and storage. These constitute respectively an electronic controller (11), a data storage register (12) and a data communication controller (13) which together make up an electronic control unit for example in the form of a suitable chip; test indicators in the form of a visual indicator (14) and audible indicator (15); and a data input means (17) to enable the input of additional data about the test. The electronic control unit may include other features such as a clock/calendar function, basic data concerning the protocol etc.

Figure 2:
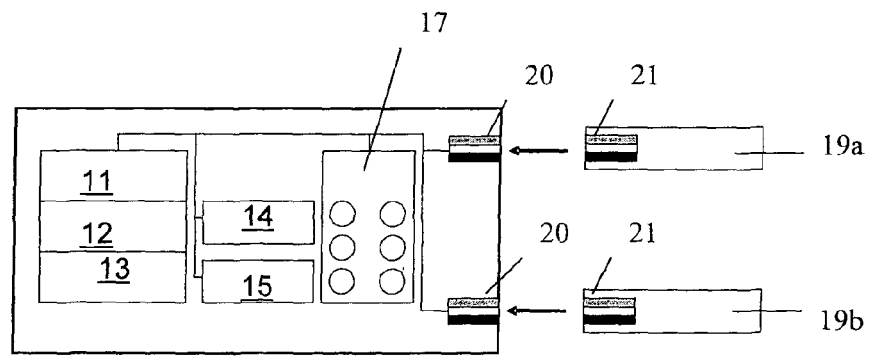
FIG. 2 is a schematic of a second alternative arrangement of device.

FIG. 2 represents a simple schematic of another possible embodiment of the invention. In this embodiment, a device that provides for a test protocol involving two blood tests spaced apart by a suitable time interval at the commencement of which a standard glycaemic load will be ingested is shown. Separate areas are provided for the placement of each test sample. Most of the components in this schematic representation are equivalent, and like reference numerals are used to refer to them.

The difference in this schematic representation is that the test zones are provided by removable test strips, respectively (19a) and (19b) for performing tests prior to and subsequent to expiry of the predetermined time period. These strips may be supplied separately, and are attachable to the body of the test device via sockets (20) which receive a portion of the test strip provided with data connectors (21). In this way, when a test strip is assembled in situ a sample receiving area (not shown) on the strip is in data communication with the remaining data modules on the device, but after performance of the test the strip can be removed. Each test strip contains reagents required for the performing of a glucose test. Said reagents may be in the form of an electrochemical biosensor.

Figure 3:
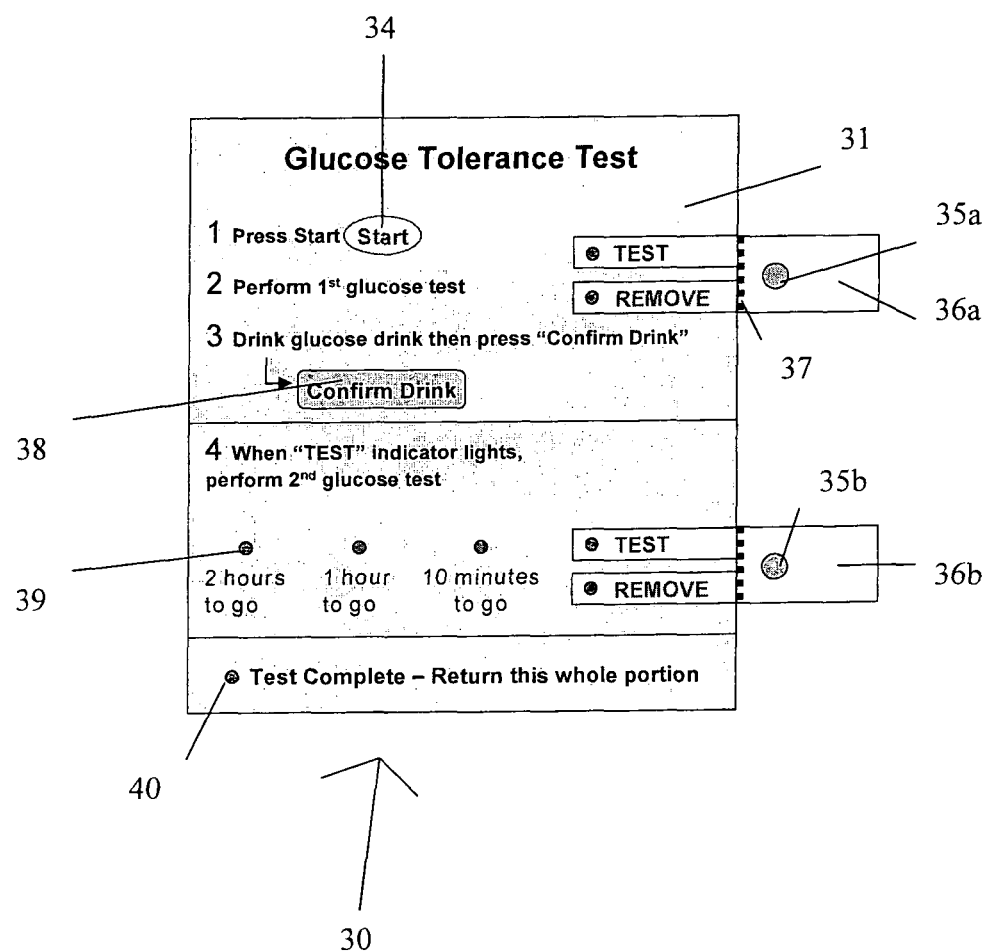
FIG. 3 is an illustration of an embodiment of device in plan view.

FIG. 3 represents an illustration of a specific device of an embodiment of the invention shown in plan view. This embodiment is closer in principle to the schematic representation in FIG. 2, in that it includes removable sample collection areas, although these are in the form of a strips which are originally fabricated integrally but to be torn off after use, rather than strips which are fabricated separately for attachment.

The device in this embodiment comprises a laminated cardboard sheet (30). The sheet may be folded prior to use, for example for compactness during storage, but is shown in an unfolded configuration.

The sheet has a water resistant surface layer, and includes basic printed instructions on its face which co-operate with features incorporated into the sheet to assist a user in performing the test protocol correctly.

The test protocol for this embodiment is a two test protocol, with first and second tests separated by a suitable time interval, the first test performed after fasting, and the second test performed a predetermined time interval after ingestion of a glucose drink.

The test device includes suitable control electronics, which are not shown in the representation of FIG. 3, but which would for example parallel those in the previous schematic diagrams, and a suitable power source such as a small battery.

The test device includes a start button (34), for example comprising paired opposing conductors which are brought into contact to close a circuit by depression of the button area, which allows a user to start the test. A finger prick blood sample is then applied to a sample receiving area (35a) on a test strip (36a). Adjacent to the strip is an "add sample" indicator LED which illuminates at the start of the test, and a "remove" indicator LED, which illuminates at the end of the test, at which point data has been suitably collected, and the whole strip (36a) can be torn away and discarded via the perforation (37).

The user then consumes a glucose drink, and presses a "confirm drink" button (38), again taking the form of paired opposing conductors which serve to close a switching circuit when the button area is depressed. The device, in response to either the pressing of the "confirm drink" button or the completion of the first blood test procedure, starts to time the necessary delay period between first and second tests. Progress of this delay period is indicated by successive illumination of LEDs (39), and once the time period has expired an audio alarm (not shown) also sounds. At this point, the second blood test is performed by applying a blood sample to a sample receiving area (35b) on a second strip (36b). Again, LEDs indicate when the test should be performed, and when the strip can be removed.

On completion of the protocol, a "test complete" LED (40) illuminates and the main portion of the device (31) can be forwarded to allow the data to processed. The test strips (36a and 36b) which contain the used blood samples have been removed from the device during the protocol and the device can thus be handled and transported safely in its entirety. In an alternative to the illustrated embodiment, the device portion (31) could be further subdivided providing a detachable sub-portion containing a data recording chip or the like, and this can be transported. Of course, other ways of processing the raw data collected by the basic device in accordance with the basic method, whether by a user or remotely, can be readily envisaged.

The embodiment of FIG. 3 is an example only of a possible device exploiting the principles of the invention. Other embodiments will readily suggest themselves, and will typically be expected to embody some and preferably all of the following basic device features:

(i) a means of performing two or more separate blood glucose measurements, said measurements being performed at predetermined time intervals, said time intervals being selected to facilitate a glucose tolerance test protocol for the investigation of impaired glucose tolerance;

(ii) an electronic control means to (a) collect and record test data and other information relating to blood glucose measurements performed using the present device (b) determine the time each glucose measurement has been performed using the present device such that the time intervals between individual glucose measurements performed using the present device may be subsequently calculated (c) optionally calculate the time intervals between individual glucose measurements performed using the present device;

(iii) a means of data communication to enable (a) data and other information to be optionally entered into and stored within the present device prior to its use for performing two or more separate blood glucose measurements (b) test data and other information to be retrieved from the present device;

(iv) visual and/or audible indication means to
(a) facilitate the correct use of the present device by informing the user of the operational status of the present device
(b) facilitate a glucose tolerance test protocol performed using the present device for the investigation of impaired glucose tolerance by informing the user of the operational status of the device and by prompting the user of key activities required to perform said test;

(v) an optional input means enabling information to be entered into and stored within the device to facilitate
(a) the collection as part of the test procedure of clinically useful information specific to a person undergoing a glucose tolerance test for the investigation of impaired glucose tolerance
(b) information useful to determine that a glucose tolerance test for the investigation of impaired glucose tolerance performed using the present device has been performed correctly.

A suitable test kit including a suitable protocol for use with the device of the illustrated embodiments might therefore include some or all of the following:

(i) a test device according to the present glucose tolerance test device specification;
(ii) a standardised glycaemic load, containing a specific and known amount of a predefined glycaemic substance, for example glucose, wherein
(a) said standardised glycaemic load is in the form of a pre-packaged drink, or
(b) said standardised glycaemic load is in the form of a powder which is to be added to a specified volume of water to produce a think, or
(c) said standardised glycaemic load is incorporated into a solid foodstuff;
(iii) a means of obtaining a blood sample, for example lancets for obtaining a finger prick blood spot;
(iv) a test procedure in which a test user is intended to perform some or all of the following steps in chronological order:
(a) fast for a specified time period, for example at least 8 hours fasting overnight, as specified by instructions accompanying present glucose tolerance test device or by the instructions of an advising medical or other practitioner,
(b) obtain a blood spot sample and add this to a first test zone on the present glucose tolerance test device,
(c) ingest the standardised glycaemic load,
(d) optionally, press a "confirm glycaemic load" button or sensor located on the present glucose tolerance test device,
(e) wait for a pre-determined time, as indicated by the present glucose tolerance test device and its accompanying instructions or by the instructions of an advising medical or other practitioner,
(f) on expiration of the pre-determined wait time, as indicated by the present glucose tolerance test device and its accompanying instructions or by the instructions of an advising medical practitioner, obtain a second blood sample in the manner of the former first blood sample and add this to a second test zone on the present glucose tolerance test device,
(g) optionally, immediately on expiration of one or more further predetermined wait times, as indicated by the present glucose tolerance test device and its accompanying instructions or by the instructions of an advising medical practitioner, obtain further blood samples in the manner of the former first blood sample and add each further blood sample in turn to further test zones on the present glucose tolerance test device,
(h) wait for a pre-determined time until the present glucose tolerance test device has concluded the test procedure, as indicated by the present glucose tolerance test device and/or its accompanying instructions or by the instructions of an advising medical practitioner.

The test procedure may incorporate the some or all of following actions performed by the present glucose tolerance test device:

(a) optionally, recording the time and optionally the date, of an event in which the present glucose tolerance test device was started or otherwise activated by a user, for example by pressing a start button or sensor,
(b) recording the time and optionally the date of the addition of a first blood sample by a user to a first test zone of the present glucose tolerance test device
(c) optionally, recording the time and optionally the date of the activation by the user of a "confirm glycaemic load" button or sensor of present glucose tolerance test device,
(d) optionally, recording the activation by the user of a "confirm glycaemic load" button or sensor which may be located on the present glucose tolerance test device,
(e) recording the time and optionally the date of the addition of a second blood sample by a user to a first test zone of the present glucose tolerance test device
(l) recording the time and optionally the date of the addition of one or more further blood samples by a user to one or more further test zones of the present glucose tolerance test device,
(g) recording the raw test data from each and every glucose test procedure performed using the test zones of the present glucose tolerance test device. For example recording test signals at pre-determined time intervals, such as micro-amps each second for 20 seconds; recording the temperature of the present glucose tolerance test device at the time when each test signal reading was obtained.

The test procedure may include a step prior to the provision of the present glucose tolerance test device to a user or other person for the purposes of assessing a particular person's glucose tolerance status by performing a glucose tolerance test on said person wherein:

(a) information relating to a unique ID and/or to a production batch reference number of the manufacturing batch of a of a particular individual present glucose tolerance test device is written to and stored within a present glucose tolerance test device, to facilitate subsequent identification of the correct calibration information to be used to process uncalibrated test data and other information retrieved from a present glucose tolerance test device, and
(b) information required to identify within a database or other record system a particular person who has been issued a particular individual present glucose tolerance test device for the purpose of performing a glucose tolerance test device is written to and stored within a present glucose tolerance test device, to facilitate matching the correct test data and other information from a particular individual present glucose tolerance test device to said particular person for the purposes of recording said person's test data and test results in a manner that can be related to said person; for example storing said person's test results within said person's health record or alternatively information relating to a unique ID of a of a particular individual present glucose tolerance test device is retrieved from said present glucose tolerance test device and stored within a database or other record system and related to a particular person who is to be provided said particular individual present glucose tolerance test device for the purpose of performing a glucose tolerance test, to facilitate matching the correct test data and other information from said particular individual present glucose tolerance test device to said particular person for the purposes of recording said person's test data and test results in a manner that can be related to said person; for example storing said person's test results within said person's health record.

In a step subsequent to the conclusion of the test procedure by the present glucose tolerance test device the information recorded by the present glucose tolerance test device maybe retrieved into a database or other form of computer software system for the purposes of:

(a) evaluating the timings of the various events recorded by the present glucose tolerance test device,
(b) processing the raw test data recorded by the present glucose tolerance test device, using selected calibration information which is specific to the particular batch identity or individual identity of the present glucose tolerance test device, in order to obtain a calibrated test result for each glucose test performed by the present glucose tolerance test device,
(c) presenting each calibrated glucose test result in chronological order,
(d) calculating and presenting the time interval between each chronologically ordered calibrated glucose test result,
(e) assessing the collected glucose test results to determine the glucose tolerance status of the test user or the subject who provided the blood for testing.

The data may be downloaded to the database in any suitable way, for example by the device facilitating connection by a user to a suitable electronic download means, or by being provided in two parts to allow a data recording part to be physically forwarded to a database manager in the manner above described.

In accordance with the foregoing, a device of the invention facilitates performance by a user in a non-clinical environment and with reduced clinical supervision of a simple standard glucose tolerance test protocol, in order to collect raw data concerning glucose tolerance in a simple and effective manner and in a format which is readily available to a supervising practitioner for subsequent analysis, for example as part of a diagnostic process. In particular, the device enables the data necessary for the clinician to make the diagnosis to be collected in a non-clinical environment, for example at home, minimising inconvenience to the patient, and then to be forwarded simply and effectively for subsequent processing, so that clinical intervention is necessary only in performance of those steps where the expertise of the clinician is particularly required. Alternatively the device can be used within a clinical setting, where the overall test protocol may be supervised by a nurse but where the test device eliminates the requirement for blood samples to be collected and tested or sent for testing by the clinic's personnel, with the test device also administering and controlling the timing of the test protocol and the performing of the blood tests separately for each patient being tested at the clinic.

The invention claimed is:

1. A test data collection device for testing glucose tolerance comprising:
   a plurality of test zones, each having a means to receive a blood test sample spaced apart by a predetermined time interval;
   a timer to measure such a time interval, and for example to measure elapsed time after collection of a said first sample;
   an indicator to indicate at least that a second test is due, operatively linked to the timer so as to make such indication after lapse of a predetermined time interval;
   a data collector to collect data from each test zone in relation to each test sample;
   a data register to store data in relation to each test sample, in data communication with the said data collector.

2. A device according to claim 1, wherein said device consists of two test zones.

3. A device according to claim 1, wherein said test zones are integral to the device.

4. A device according to claim 1, wherein raw test data are stored in said data register for calibration externally in a separate instrument.

5. A device according to claim 4, further comprising means to measure and store the temperature of the device or its environment when measurements are made.

6. A device according to claim 4, further comprising a unique identification code that may be used to identify a particular individual using the device.

7. A device according to claim 1, wherein said data storage part is detachable.

8. A test data collection device for testing glucose tolerance comprising:
   a plurality of test zones, each having a means to receive a blood test sample spaced apart by a predetermined time interval, each of said test zones fabricated integral with said device and adapted to be torn away from the device after use;
   a timer to measure such a time interval, and for example to measure elapsed time after collection of a said first sample;
   an indicator to indicate at least that a second test is due, operatively linked to the timer so as to make such indication after lapse of a predetermined time interval;
   a data collector to collect data from each test zone in relation to each test sample;
   a data register to store data in relation to each test sample, in data communication with the said data collector.

9. A device as claimed in claim 8, whereas each of said test zones comprise a test strip containing a reagent for performing a glucose test, each said test strip affixed to, and extending from, said device for manually gripping and tearing away from the device after use.

10. A method of collecting data for performance of a glucose tolerance test in which a user carries out the following steps:
    fasts for a specified time period;
    obtains a test device in accordance with claim 1;
    adds a first blood spot sample to a test zone on the test device to obtain a first result;
    ingests a standardized glycaemic load;
    optionally following ingestion of a standardized glycaemic load operates a user operable control to indicate the start of a predetermined time interval;
    waits a predetermined time interval before performing at least one further blood test by adding at least one further blood sample to a test zone on the test device to obtain a further result.

11. The method of claim 10, including the further step of supplying data collected for final analysis in that the device comprises detachable collecting part and recording part, and the method comprises detaching the recording part and forwarding the same for analysis of the data.

* * * * *